(12) United States Patent
McLawhorn et al.

(10) Patent No.: US 9,844,407 B2
(45) Date of Patent: Dec. 19, 2017

(54) BIPOLAR SPHINCTEROTOME

(71) Applicant: Cook Medical Technologies LLC, Bloomington, IN (US)

(72) Inventors: Tyler Evans McLawhorn, Winston-Salem, NC (US); Vihar C. Surti, Winston-Salem, NC (US); John Crowder Sigmon, Jr., Winston-Salem, NC (US); Michelle D. Martinez, Winston-Salem, NC (US); Jillian Haac, Winston-Salem, NC (US); Shaun D. Gittard, Winston-Salem, NC (US); Richard B. Sisken, West Lafayette, IN (US); Richard W. Ducharme, Pleasant Gap, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 111 days.

(21) Appl. No.: 14/139,214

(22) Filed: Dec. 23, 2013

(65) Prior Publication Data

US 2014/0188109 A1    Jul. 3, 2014

Related U.S. Application Data

(60) Provisional application No. 61/746,162, filed on Dec. 27, 2012.

(51) Int. Cl.
*A61B 18/14* (2006.01)
*A61B 18/16* (2006.01)
(Continued)

(52) U.S. Cl.
CPC ........ *A61B 18/1482* (2013.01); *A61B 18/149* (2013.01); *A61B 18/16* (2013.01);
(Continued)

(58) Field of Classification Search
CPC ...... A61B 2018/126; A61B 2018/1407; A61B 2018/141; A61B 2018/144;
(Continued)

(56) References Cited

U.S. PATENT DOCUMENTS

| | | |
|---|---|---|
| 1,983,669 A | 12/1934 | Kimble |
| 2,056,377 A | 10/1936 | Wappler |

(Continued)

FOREIGN PATENT DOCUMENTS

| | | |
|---|---|---|
| DE | 2426781 | 12/1975 |
| DE | 3315303 | 11/1984 |

(Continued)

OTHER PUBLICATIONS

Invitation to Pay Additional Fee for corresponding application No. PCT/US2014/068272 dated Feb. 18, 2015.
(Continued)

*Primary Examiner* — Jaymi Della
(74) *Attorney, Agent, or Firm* — Brinks Gilson & Lione

(57) ABSTRACT

A bipolar sphincterotome may include an elongate tubular member, a cutting wire, and a return path. The return path may include a conductive ink portion disposed on an outer surface at a distal portion of the tubular member. The return path may also include a return wire disposed within the tubular member that is electrically coupled to the conductive ink portion. In some example embodiments, the return wire may be disposed within a lumen configured to have two or more functions, one of which being to house the return wire. Additionally, in some example embodiments, the conductive ink portion may be circumferentially disposed on the outer surface to provide visual access to a wire guide lumen. Also, for some example embodiments, the bipolar sphincterotome may include two electrically isolated return paths.

20 Claims, 7 Drawing Sheets

(51) Int. Cl.
    *A61B 17/00* (2006.01)
    *A61B 18/00* (2006.01)
    *A61B 90/90* (2016.01)
(52) U.S. Cl.
    CPC ......... *A61B 90/90* (2016.02); *A61B 2017/003* (2013.01); *A61B 2018/00148* (2013.01); *A61B 2018/00166* (2013.01); *A61B 2018/00553* (2013.01); *A61B 2018/00601* (2013.01); *A61B 2018/1407* (2013.01); *A61B 2018/1475* (2013.01); *A61B 2018/162* (2013.01); *A61B 2018/165* (2013.01)
(58) Field of Classification Search
    CPC ...... A61B 2018/162; A61B 2018/1497; A61B 2018/1492; A61B 2018/1475; A61B 18/49; A61B 2018/165; A61B 18/16
    See application file for complete search history.

(56) References Cited

U.S. PATENT DOCUMENTS

| | | | |
|---|---|---|---|
| 4,476,862 A | 10/1984 | Pao | |
| 4,823,791 A | 4/1989 | D'Amelio et al. | |
| 5,007,908 A | 4/1991 | Rydell | |
| 5,035,696 A * | 7/1991 | Rydell | A61B 18/14 606/47 |
| 5,201,732 A | 4/1993 | Parins et al. | |
| 5,254,121 A | 10/1993 | Manevitz et al. | |
| 5,462,545 A * | 10/1995 | Wang | A61B 18/1492 600/373 |
| 5,480,399 A * | 1/1996 | Hebborn | A61B 18/16 128/908 |
| 5,810,807 A * | 9/1998 | Ganz | A61B 18/1492 606/113 |
| 5,925,045 A | 7/1999 | Reimels et al. | |
| 5,944,715 A | 8/1999 | Goble et al. | |
| 5,991,650 A * | 11/1999 | Swanson | A61B 5/0422 374/E1.005 |
| 6,027,501 A | 2/2000 | Goble et al. | |
| 6,032,061 A * | 2/2000 | Koblish | A61L 29/085 600/372 |
| 6,071,281 A * | 6/2000 | Burnside | A61B 18/1482 606/37 |
| 6,097,976 A | 8/2000 | Yang et al. | |
| 6,440,128 B1 | 8/2002 | Edwards et al. | |
| 6,443,924 B1 * | 9/2002 | Rowland | A61B 18/10 604/96.01 |
| 6,471,702 B1 * | 10/2002 | Goto | A61B 18/14 606/46 |
| 6,514,248 B1 | 2/2003 | Eggers et al. | |
| 6,712,817 B1 | 3/2004 | Goto et al. | |
| 7,879,030 B2 | 2/2011 | Paul et al. | |
| 8,142,431 B2 | 3/2012 | Ducharme | |
| 2002/0049423 A1 * | 4/2002 | Howell | A61B 18/14 604/528 |
| 2002/0095152 A1 | 7/2002 | Ciarrocca et al. | |
| 2003/0114849 A1 | 6/2003 | Ryan | |
| 2003/0181900 A1 | 9/2003 | Long | |
| 2004/0015162 A1 * | 1/2004 | McGaffigan | A61B 18/1206 606/34 |
| 2005/0119654 A1 | 6/2005 | Swanson et al. | |
| 2005/0203441 A1 | 9/2005 | Voegele | |
| 2010/0057077 A1 | 3/2010 | Ducharme | |
| 2012/0071870 A1 * | 3/2012 | Salahieh | A61B 5/01 606/33 |
| 2012/0089141 A1 | 4/2012 | Lee et al. | |
| 2012/0123411 A1 | 5/2012 | Ibrahim et al. | |
| 2012/0310265 A1 | 12/2012 | Martinez | |

FOREIGN PATENT DOCUMENTS

| | | |
|---|---|---|
| EP | 0440 385 A2 | 8/1991 |
| EP | 0 959 786 | 12/1999 |
| JP | 7-51288 A | 2/1995 |
| JP | 2008-529610 A | 8/2008 |
| WO | WO 97/48345 | 12/1997 |
| WO | WO 2006/084316 A1 | 8/2006 |

OTHER PUBLICATIONS

Invitation to Pay Additional Fee for corresponding application No. PCT/US2013/077800 dated Mar. 25, 2014.
International Search Report and Written Opinion for corresponding application No. PCT/US2014/068272 dated Apr. 8, 2015.
International Search Report and Written Opinion for corresponding application No. PCT/US2013/077800 dated Jun. 11, 2014.
Jerome H. Siegel, M.D. et al, "Bipolar Versus Monopolar Sphincterotomy: A Prospective Trial", The American Journal of Gastroenterology, vol. 89, No. 10, 1994, pp. 1827-1830.
Robert D. Tucker, M.D. et al., "Bipolar Electrosurgical Sphincterotomy", The American Society for Gastrointestinal Endoscopy, vol. 38, No. 2. 1992, pp. 113-117.
Office Action, and English language translation thereof, in corresponding Japanese Application No. 2015-550765, dated Jun. 15, 2016, 9 pages.
Office Action in corresponding U.S. Appl. No. 14/560,563, dated Feb. 7, 2017, 15 pages.

* cited by examiner

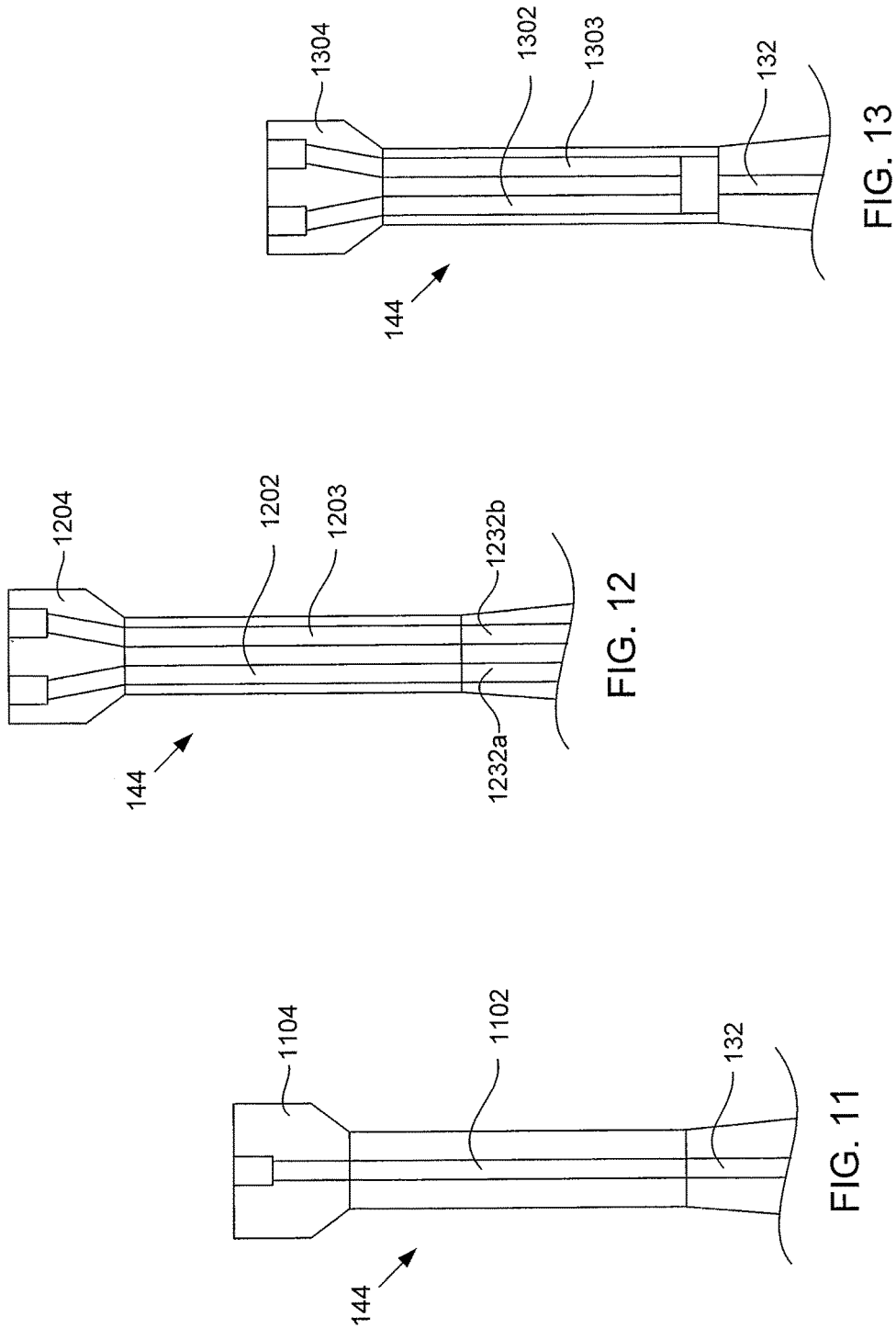

BIPOLAR SPHINCTEROTOME

CROSS-REFERENCE TO RELATED APPLICATION

The present application claims the benefit of U.S. Provisional Application No. 61/746,162, filed Dec. 27, 2012. The contents of U.S. Provisional Application No. 61/746,162 are hereby incorporated by reference in their entirety.

TECHNICAL FIELD

The present invention relates generally to medical devices, and more particularly to bipolar sphincterotomes.

BACKGROUND

A sphincterotome is a medical device that is used to perform a sphincterotomy, which involves cutting a sphincter muscle, such as the sphincter of Oddi. The sphincter muscle may need to be cut to relieve its constrictive nature and allow one or more medical devices through the muscle. For example, problems occurring in the biliary tree, such as the formation of bile duct stones or papillary stenosis, may be treated using medical devices that are delivered into the biliary tree. In order to access the biliary tree, the medical devices may pass through the sphincter of Oddi. To facilitate passage of the medical devices through the sphincter of Oddi, the sphincter muscle may be cut using a sphincterotome.

A sphincterotome may generally include an elongate tubular member, such as a catheter, and a cutting wire that is used to cut the sphincter muscle. The cutting wire may extend through a lumen of the catheter, except at a distal portion of the catheter, where the cutting wire may project from and be exposed outside of the catheter. The exposed portion, which may be referred to as a cutting edge, may be used to cut the sphincter muscle.

A sphincterotomy generally involves a two-part process: cannulation of the biliary tree and cutting the sphincter muscle by sending electric current through the cutting wire (i.e, electrosurgery). Cannulation of the biliary tree may include inserting the distal portion of the catheter into the papilla and using the distal portion and the cutting edge to lift an upper portion (i.e., the roof) of the papilla. The roof of the papilla may be lifted by proximally pulling the cutting wire taut, causing the distal portion of the tubular member to bow and form an arc. After cannulation, the electric current may be provided to the cutting edge to cut the sphincter muscle.

BRIEF SUMMARY

In a first aspect, a bipolar sphincterotome to perform a sphincterotomy at a treatment site is provided. The bipolar sphincterotome includes an elongate tubular member; a cutting wire disposed within the tubular member; and a return path. The return path includes a conductive material portion disposed on an outer surface at a distal portion of the tubular member, and a return wire electrically coupled to the conductive material portion, where the return wire is disposed within the tubular member. The conductive material portion may have a circumferential disposition on the outer surface that provides visual access to a wire guide lumen extending within the tubular member.

In a second aspect, a bipolar sphincterotome to perform a sphincterotomy at a treatment site within a patient is provided. The bipolar sphincterotome includes an elongate tubular member; a cutting wire disposed within the tubular member, except for a cutting edge of the cutting wire, where the cutting edge protrudes from the tubular member; a first return path; and a second return path substantially electrically isolated from the first return path. The first return path includes a first return wire, and the second return path comprises a second return wire. The first and second return wires longitudinally extend within the tubular member from a distal portion to a proximal portion of the tubular member.

In a third aspect, a method of adhering conductive ink to an outer surface of an elongate tubular member of a medical device, the elongate tubular member comprising polytetrafluoroethylene, is provided. The method includes: applying a primer ink to the outer surface of the elongate tubular member; and applying the conductive ink over the primer ink.

BRIEF DESCRIPTION OF THE DRAWINGS

FIG. 11. shows a cross-sectional view of cabling electrically coupling a single return wire with a single wire in the cabling.

FIG. 12. shows a cross-sectional view of an alternative embodiment of the cabling of FIG. 11, where the cabling includes two wires, each electrically coupled to a return wire.

FIG. 13 shows a cross-sectional view of a second alternative embodiment of the cabling of FIG. 11, where the cabling includes two wires shorted together and electrically coupled to a single return wire.

DETAILED DESCRIPTION

The present disclosure describes various embodiments of a sphincterotome having a bipolar configuration, otherwise referred to as a bipolar sphincterotome. Sphincterotomes may include an elongate tubular member, such as a catheter, and a cutting wire used to cut a sphincter muscle when performing a sphincterotomy. The cutting wire may be coupled to and/or in electrical communication with a radio frequency (RF) generator, such as an electrosurgical unit (ESU). When the RF generator is activated, the RF generator may supply electrical current to the cutting wire, which may cut the sphincter muscle. The electrical current may travel along the cutting wire, through the sphincter muscle, and then along a return path, which completes the circuit.

The return path for sphincterotomes having a monopolar configuration may include a neutral electrode, which may be a solid, neutral electrode, or a split neutral electrode, and which may be positioned on the thigh of the patient undergoing the sphincterotomy. The return path for bipolar sphincterotomes may differ from monopolar sphincterotomes in that, like the cutting wire (i.e., the active path), the return path may be attached to, integrated with, disposed within, or included as part of the catheter.

Figure 1:
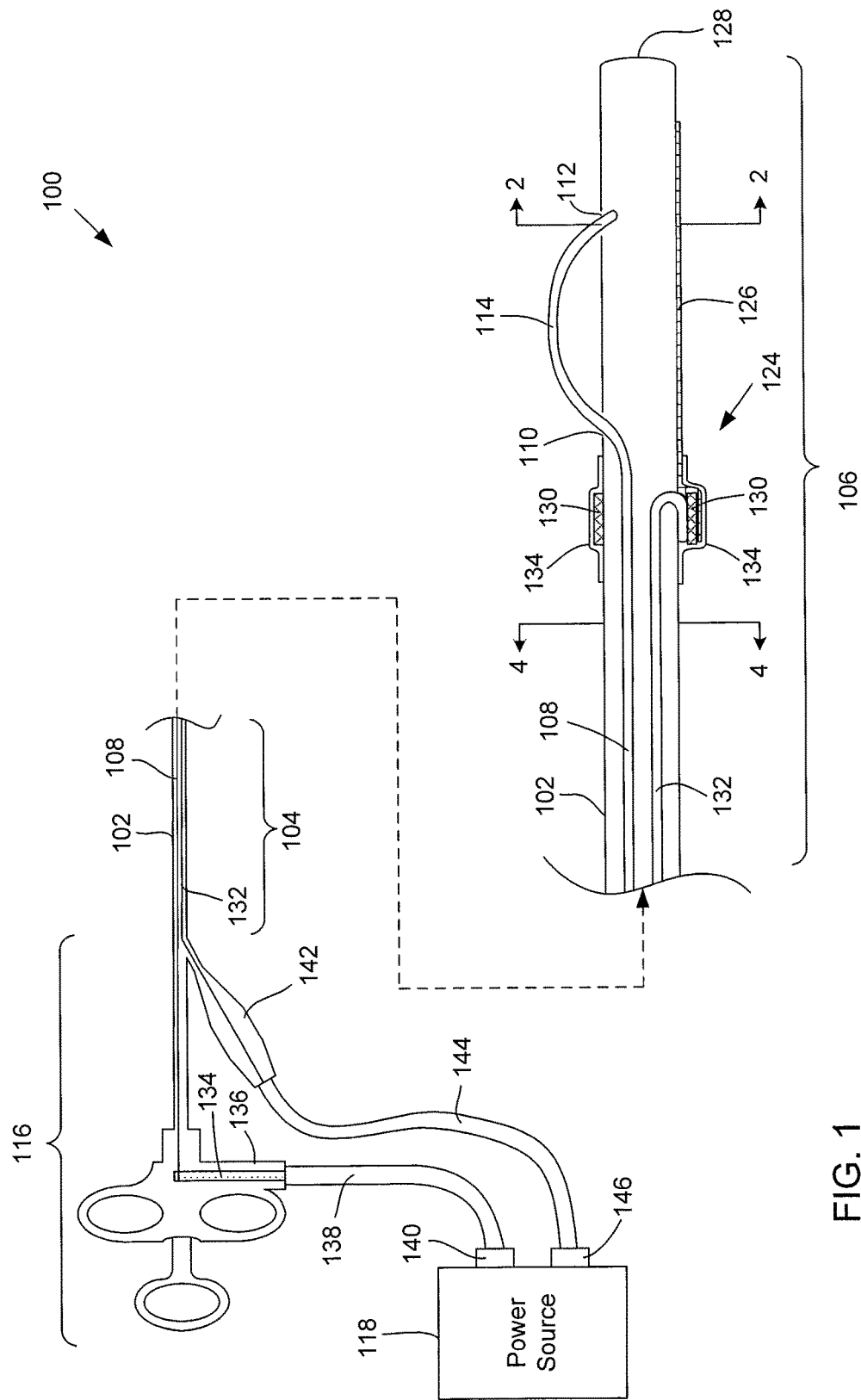
FIG. 1 shows a cross-sectional side view of a bipolar sphincterotome.

FIG. 1 shows a partially cross-sectional side view of an example bipolar sphincterotome 100. The example bipolar sphincterotome 100 may include an elongate, tubular member 102 that has a proximal portion 104 extending to a distal portion 106. A cutting wire 108 used to cut the sphincter muscle may be disposed within a lumen (not shown in FIG. 1) of the tubular member 102 from the proximal portion 104 to the distal portion 106. At the distal portion 106, the cutting wire 108 may extend or protrude from within the tubular member 102, through a first opening 110 of the tubular member 102, to outside the tubular member 102. Outside the tubular member 102, the cutting wire 108 may longitudinally extend substantially parallel with the tubular member 102 to a second opening or anchor point 112 of the tubular member 102 that is distal the first opening 110, where a distal end of the cutting wire 108 may re-enter and/or be fixedly attached to the tubular member 102. The exposed portion 114 of the cutting wire 108 may be referred to as a cutting edge, which may be the portion of the cutting wire 108 that cuts the sphincter muscle.

The bipolar sphincterotome 100 may further include a return path 124. For the bipolar configuration, the return path 124 may be attached to, adhered to, integrated with, disposed within, or included as part of the tubular member 102. In the example embodiment of the bipolar sphincterotome 100, the return path 124 may include conductive material portion 126 disposed on or cover an outer surface of the distal portion 106 of the tubular member 102, and a return wire 132 electrically coupled to the conductive ink portion 126.

In one example embodiment of the return path 124, the conductive material portion 126 may be made of conductive ink. The conductive material portion 126 is hereafter referred to as a conductive ink portion 126, although conductive materials other than ink may be used. The conductive ink portion 126 may be attached to an outer surface of the tubular member 102 at the distal portion 106. In some example embodiments, the conductive ink (or alternatively referred to as conductive paint or conductive coating) making up the conductive ink portion 126 may have a thickness in a range of about 20-40 micrometers (microns), although other thicknesses may be used, including up to 500 microns. Particles of the conductive ink may have a size in a range of about 3-30 microns. Also, the particles may be made of silver and/or may be suspended in a polyester binder. Additionally, the conductive ink may have a viscosity of about 250 centipoise (cP), although other viscosities may be used, including up to about 10,000 cP. Also, a resistance of the conductive ink portion 126 may be in a range of about zero (or substantially zero) to ten Ohms, when measured longitudinally. An example conductive ink, which may or may not include all of the above-described properties, may be AG-510 Silver Filled Electrically Conductive Screen Printable Ink/Coating by Conductive Compounds, Inc.

The conductive ink portion 126 may extend distally past the anchor point 112. Extending the conductive ink portion 126 distally past the anchor point 112 may ensure or increase the likelihood that the return path 124 contacts the sphincter muscle (or tissue near the sphincter muscle) to make a proper connection at the treatment site. Additionally, the conductive ink portion 126 may distally extend to a position before a distal tip 128 or sufficiently away from an opening of a wire guide lumen (not shown in FIG. 1) at the distal tip 128 so that a wire guide in the wire guide lumen is not part of or is isolated from the return path 124. In addition, the conductive ink portion 126 may proximally extend past the first opening 110.

Figure 4:
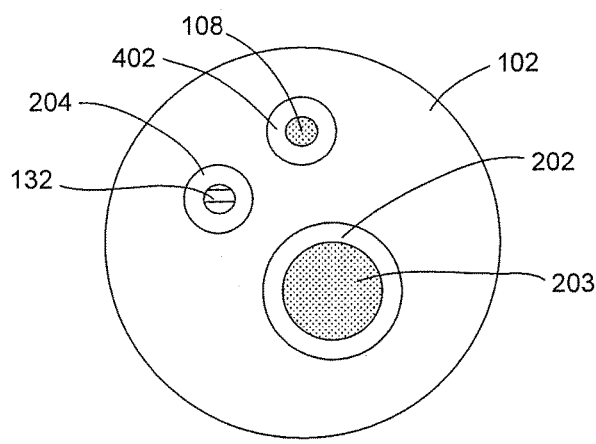
FIG. 4 shows a cross-sectional axial view of the bipolar sphincterotome of FIG. 1 taken proximal a coupling area of a return path, showing a return wire disposed in a lumen having multiple functions.
Figure 5:
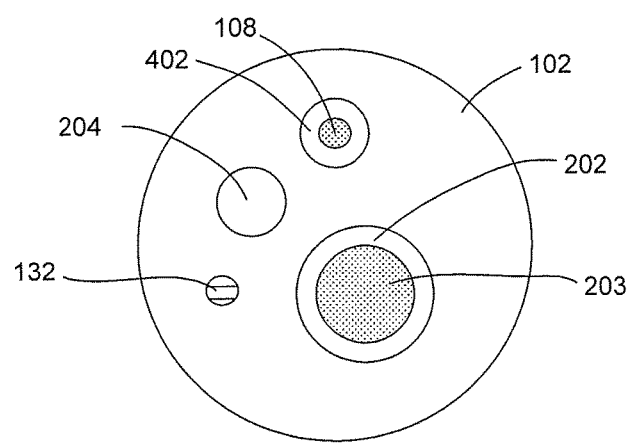
FIG. 5 shows a cross-sectional axial view of an alternative embodiment of the cross-section of the bipolar sphincterotome shown in FIG. 4, where the return wire is embedded in a tubular member of the bipolar sphincterotome.
Figure 6:
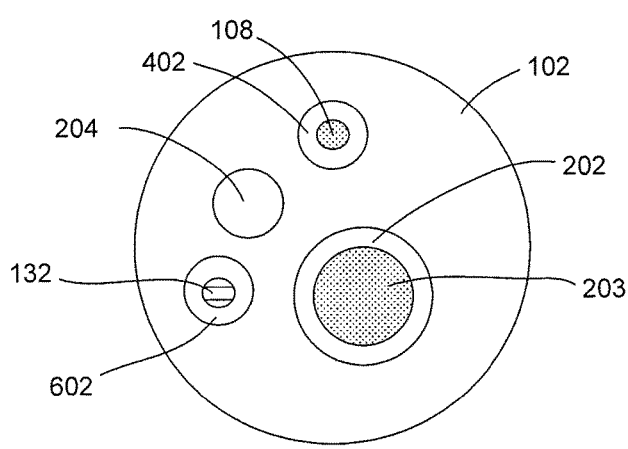
FIG. 6 shows a cross-sectional axial view of another alternative embodiment of the cross-section of the bipolar sphincterotome shown in FIG. 4, where the return wire is disposed in a lumen having a sole function to house the return wire.

The conductive ink portion 126 may be electrically coupled to a return wire 132, which may form and/or be part of the return path 124. The return wire 132 may extend within the tubular member 102 from where the return wire 132 is electrically coupled to the conductive ink portion 126 to the proximal portion 104. The return wire 132 may extend within the tubular member 102 generally or substantially parallel to the cutting wire 108. In addition, the return wire 132 may extend within the tubular member 102 in various locations relative to the cutting wire 108. FIG. 1 shows the active wire 108 and the return wire 132 generally in the same cross-sectional plane. However, as shown in FIGS. 4-6, the return wire 132 may be disposed within the tubular member 102 in various locations relative to the cutting wire 108. Also, as described in more detail below, the return wire 132 may be disposed and/or extend within a lumen of the tubular member 102, or alternatively, may be embedded within and/or coextruded with the tubular member 102.

The conductive ink portion 126 may be electrically coupled to the return wire 132 in various ways. For example, as shown in FIG. 1, the conductive ink portion 126 may proximally extend to a conductive ring or cannula 130, which may electrically couple the conductive ink portion 126 to the return wire 132. In some example embodiments, the conductive cannula 130 may be attached or crimped to the outer surface of the tubular member 102. The conductive cannula 130 may be made of metal, such as stainless steel, silver, gold, tantalum, or tungsten, as examples. The conductive ink may be applied to and/or deposited over and/or under at least a portion of the conductive cannula 130 so that the conductive ink portion 126 and the conductive cannula 130 are electrically coupled, and the conductive cannula 130 is part of the return path 124. As shown in FIG. 1, the return wire 132 may be connected to the conductive cannula 130 to be electrically coupled with the conductive ink portion 126. For example, the return wire 132 may be curled at its distal end to extend to the outer surface of the tubular member 102, and the conductive cannula may be crimped to the tubular member 102 over the distal end of the return wire 132.

In some embodiments, the bipolar sphincterotome 100 may further include a tube 134 disposed over the conductive cannula 130 and the conductive ink that is covering or disposed on the conductive cannula 130. As shown in FIG. 1, the tube 134 may distally extend to the first opening 110 in the tubular member 102, or alternatively to a position in between the cannula 130 and the first opening 110. In some embodiments, the tube 134 may be a shrink tube 134 that conforms to the surface that the shrink tube 134 is covering, such as when heat is applied to the shrink tube 134. The tube 134 may have a thickness of about 0.0002 inches, although other thicknesses may be used. The tube 134 may be disposed over the cannula 130 to provide a relief to the strain caused by varying flexibilities between the tubular member 102 (which may be relatively flexible) and the metal cannula 130 (which may be relatively rigid). Additionally, the tube 134 may provide a protective coating or scratch resistance, which may prevent or minimize the conductive ink from being scratched off.

For some example embodiments of the tube 134, an inner surface of the tube 134 may be coated with one or more conductive materials, such as a conductive ink, a conductive powder, a conductive adhesive, or combinations thereof, as examples. The conductive material may be the same material as or may be a different material then the conductive ink that makes up the conductive ink portion 126. The tube 134, with an inner surface coated with a conductive material, may enhance electrical continuity between the conductive ink portion 126 and the conductive cannula 130.

FIG. 1 shows a part of the conductive ink portion 126 disposed or deposited over the conductive cannula 130 so that the conductive ink portion 126 and the conductive cannula 130 may be electrically connected with each other. In an alternative embodiment of the distal portion 106, the conductive ink portion 126 may be deposited on the outer surface of the tubular member 102 and/or the conductive cannula 130 may be positioned relative to the conductive ink portion so that they are physically separated, and/or so that by themselves, they are electrically disconnected from each other. For this alternative embodiment, the tube 134 with an inner surface being coated with a conductive material may be disposed over both the conductive cannula 130 and the conductive ink portion 126 to electrically connect the conductive ink portion 126 with the conductive cannula 130.

In still other alternative embodiments, the tube 134 may be replaced with an adhesive, an epoxy, a notched cannula, a cannula with a wavy or flexible distal tip, or any combination thereof. In still other alternative embodiments, the tube 134 or other covering or coating may not be included.

Figure 1A:
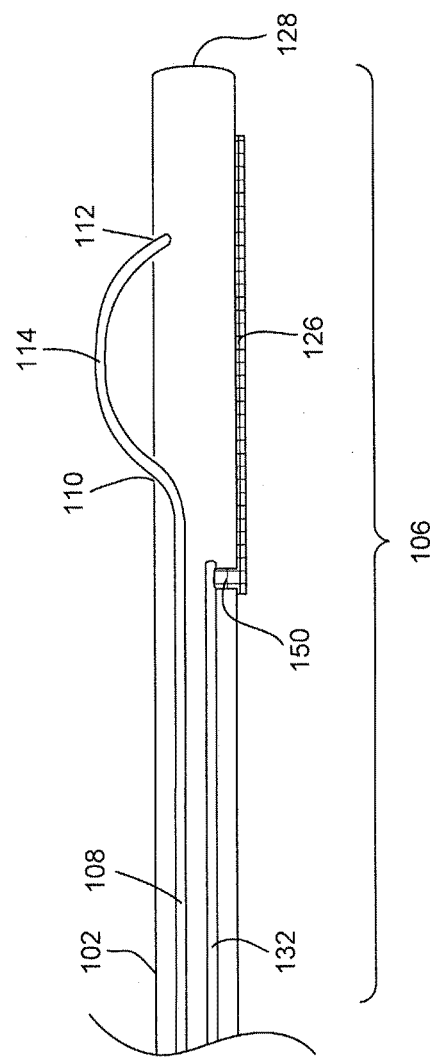
FIG. 1A shows cross-sectional side view of an alternative embodiment of a distal portion of the bipolar sphincterotome shown in FIG. 1.

Referring to FIG. 1A, another alternative example embodiment of the bipolar sphincterotome 100 may include an opening 150 in a wall of the tubular member 102 instead of the metal cannula 130 to electrically couple the return wire 132 with the conductive ink portion 126. The opening 150, such as a skive or a cut in the tubular member 102, may extend from the outer surface of the tubular member 102 to an inner portion where a distal end of the return wire 132 is disposed. The conductive ink portion 126 may be deposited to extend within the opening 150 so that the conductive ink portion 126 is electrically coupled to the return path 132.

Referring back to FIG. 1, the bipolar sphincterotome 100 may further include a handle assembly 116 coupled to the proximal portion 104 and/or a proximal end of the cutting wire 108. The handle assembly 116 may be operatively coupled to the cutting wire 108 to move the cutting edge 114 between a relaxed state and a cutting state. For example, the handle assembly 116 may be configured to move the cutting edge 114 from the relaxed state to the cutting state by proximally pulling the cutting wire 108 taut. When the cutting wire 108 is pulled, the distal portion 106 of the tubular member 102 may bow or curl, forming an arc. The taut cutting edge 114 may form a secant of the arc. When the distal portion 106 is curled and the cutting edge 114 is taut, the distal portion 106 and the cutting edge 114 may be configured or in position to cut the sphincter muscle. The handle assembly 116 may also be configured to release or distally push the cutting wire 108 to uncurl the distal portion 106 and to move the cutting edge 114 from the taut state to the relaxed state. When the distal portion 106 is uncurled (or at least in a position that is curled to a lesser degree than when the cutting edge 114 is taut) and the cutting edge 114 is in the relaxed state, the distal portion 106 and the cutting edge 114 may not be configured to cut the sphincter muscle and/or may be configured or in position to be moved to and from the treatment site.

Both the cutting wire 108 and the return wire 132 may be electrically coupled to a power source 118, such as a radio frequency (RF) generator or an electrosurgical unit (ESU), that supplies electrical current to the cutting wire 108 to perform the electrosurgery. In one example embodiment, the cutting wire 108 may be electrically coupled to the power source 118 by proximally extending to the handle assembly 116, where the proximal end of the cutting wire 108 may be connected to a metallic pin 134 that extends to a port 136 of the handle assembly 116. The metallic pin 134 and/or the port 136 may be adaptable to connect to supply cabling 138 that may connect to an active port 140 of the power source 118.

The return wire 132 may be electrically coupled to the power source 118 by distally extending through a side port 142 connected to the tubular member 102, where a proximal end of the return wire 132 may be connected to return cabling 144, such as by soldering the return wire with one or more wires of the return cabling 144. Alternatively, the return wire 132 may be connected to the return cabling 144 by crimping the return cabling to the return wire 132 disposed inside a metal cannula. The return cabling 144 may be adaptable to connect to a return port 146 of the power source 118. When the power source 118 is activated, the power source 118 may deliver electric current to the cutting wire 108 via the supply cabling 138 and the metallic pin 134. The electrical current may pass through the cutting wire 108 to the cutting edge 114, where electrosurgery may be performed on sphincter muscle. The electrical current may pass through the sphincter muscle, which acts as a load, and then along the return path 124, including the conductive ink portion 126 and the return path, back to the power source 118 via the return cabling 144.

Figure 2:
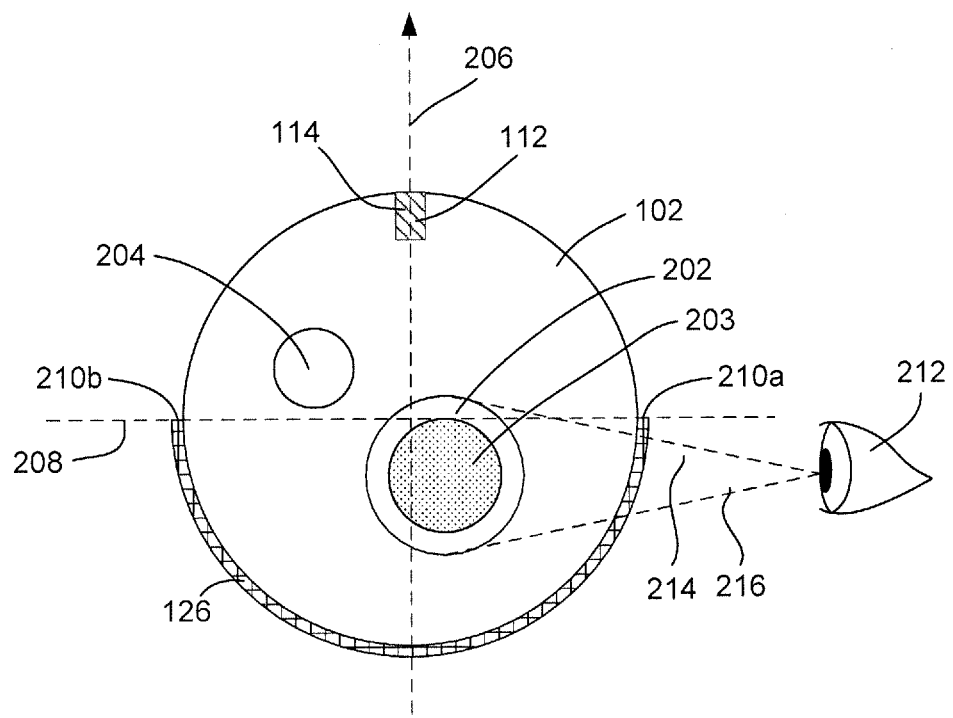
FIG. 2 shows a cross-sectional axial view of the distal portion of the bipolar sphincterotome of FIG. 1, showing a circumferential orientation of a conductive ink portion.

FIG. 2 shows a cross-sectional view of an example embodiment of the bipolar sphincterotome 100 taken along line 2-2 in FIG. 1. The tubular member 102 may include a wire guide lumen 202 that is configured to receive and have movably disposed therethrough a wire guide 203. In operation, the wire guide 203 may be delivered to the treatment site within the patient. The wire guide lumen 202 may be inserted over the wire guide 203, and the distal portion 106 of the bipolar sphincterotome 100 may be delivered to the treatment site. The tubular member 102 may include one or more other lumens, such as an injection lumen 204, which may be used to deliver contrast to the treatment site.

As shown in FIG. 2, the conductive ink portion 126 may be circumferentially disposed partially around the outer surface of the tubular member 102. The circumferential disposition of the conductive ink portion 126 may have an orientation that is defined or determined relative to a radial orientation of the anchor point 112 or the cutting edge 114 of the cutting wire 108. The radial orientation of the anchor point 112 or the cutting edge 114 may be defined by a direction in which the cutting edge 114 radially extends from the tubular member and/or may be identified by a dotted arrow 206, which extends from a center point or origin of the tubular member 102 through the anchor point 112. The orientation of the circumferential disposition of the conductive ink portion 126 may be identified by a dotted line 208 extending through the circumferential ends 210a, 210b of the conductive ink portion 126. The orientation of the circumferential disposition of the conductive ink portion 126 relative to the radial orientation of the anchor point 112 or cutting edge 114 may be defined or determined as a radial difference or difference in degrees between the dotted lines 206 and 208. In one example configuration, as shown FIG. 2, the circumferential disposition of the conductive ink portion 126 may be oriented perpendicular or substantially perpendicular to the radial orientation of the anchor point 112 or the cutting edge 114, as identified by the ninety-degree radial difference or perpendicular intersection between the dotted lines 206 and 208.

The tubular member 102 may be made of a clear, or at least semi-clear, material. The tubular member 102 may be clear or semi-clear for visualization purposes. For example, a side viewing endoscope may provide a physician or other operator of the bipolar sphincterotome 100 visual access to the side of the tubular member 102. The clear material may further provide the physician or operator visual access to inside the tubular member 102, such as visual access to one or more lumens of the tubular member 102. In particular, the clear material may provide visual access to the wire guide lumen 202 so that the physician or operator may see the wire guide 203 move through the wire guide lumen 202.

However, the conductive ink portion 126 may be an opaque or substantially opaque material, which may block or impede visual access to within the tubular member 102, and particularly the wire guide lumen 202. As such, it may be desirable to orient the conductive ink portion 126 around the tubular member 102 in a way that provides for visual access to the wire guide lumen 202. In some example tubular member configurations as shown in FIG. 2, the wire guide lumen 202 may be disposed within the tubular member 102 relative to the anchor point 112 or the wire guide 108 such that a perpendicular orientation of the circumferential disposition of the conductive ink portion 126 relative to the radial orientation of the anchor point 112 or the cutting edge 114 may block or prevent visual access to the wire guide lumen 202. FIG. 2 shows how visual access, represented by eyeball 212 and dotted lines 214, 216, may be blocked by the perpendicular orientation.

Figure 3:
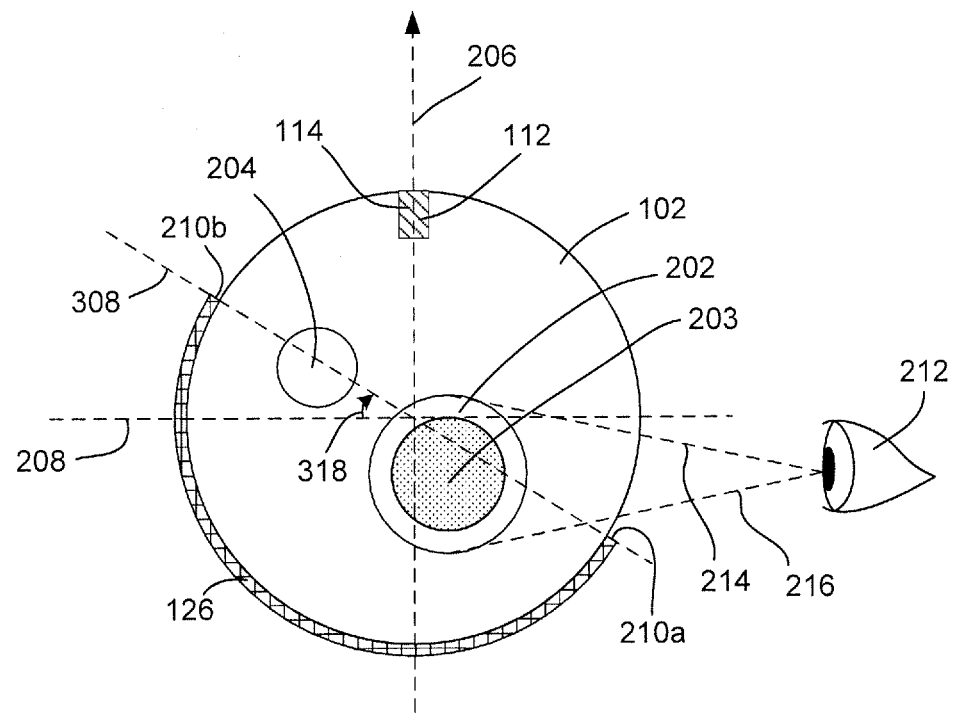
FIG. 3 shows a cross-section axial view of the distal portion of the bipolar sphincterotome of FIG. 1, showing an alternative circumferential orientation of the conductive ink portion.

FIG. 3 shows a cross-sectional view of an alternative embodiment of the bipolar sphincterotome 100 taken along line 2-2 in FIG. 1. In the alternative embodiment shown in FIG. 3, the circumferential disposition of the conductive ink portion 102 may have an orientation that is offset (denoted by dotted line 308) from the perpendicular orientation (denoted by dotted line 208) to unblock or provide visual access to the wire guide lumen 202. In some example configurations, the offset (denoted by arrow 318) may be about thirty-degrees, although any degree offset may be utilized that provides visual access to the wire guide lumen. Also, the direction in which the offset is made may depend on the side of the bipolar sphincterotome 100 to which the side viewing endoscope is configured to have visual access. For example, when looking at the cross-section of the bipolar sphincterotome 100 from the perspective shown in FIG. 3, visual access (denoted by the eyeball 212 and the dotted lines 214, 216), may be on the "right" side. As such, the offset may be in a clockwise direction. Alternatively, if visual access were on the opposite side (e.g., the "left" side from the perspective in FIG. 3), then the offset may be in a counter-clockwise direction.

FIGS. 2 and 3 show that the circumferential disposition of the conductive ink portion 126 extends about halfway around the tubular member (i.e., the dotted line 206 extends through the center or origin of the tubular member 102). In alternative configurations, the circumferential disposition of the conductive ink portion 126 may extend less than halfway or more than halfway around the tubular member.

FIG. 4 shows a cross-sectional view of an embodiment of the sphincterotome 100 taken along line 4-4 in FIG. 1. The cross-sectional view shown in FIG. 4 may be representative of the cross-section of the tubular member 102 proximal the conductive cannula 130. FIG. 4 shows the wire guide 203 disposed within the wire guide lumen, as well as the cutting wire 108 disposed within a cutting wire lumen 402. In addition, as shown in FIG. 4, the return wire 132 may be disposed and extend within the injection lumen 204. As such, the injection lumen 204 may serve a dual role or have two functions—to deliver contrast to the treatment site, and to house the return path 132 of the bipolar sphincterotome 100. Although the embodiment in FIG. 4 shows the return wire 132 disposed within the injection lumen 204, the return wire 132 may be disposed in a different lumen than the injection lumen 204. Generally, the sphincterotome 100 may be configured so that one of a plurality of lumens within the tubular member 102 has dual or multiple purposes or functions, one of which is to house the return wire 132.

FIG. 5 shows a cross-sectional view of an alternative embodiment of the bipolar sphincterotome 100 taken along line 4-4 in FIG. 1. In the alternative embodiment, the return wire 132 may be embedded within and/or an integral part of the tubular member 102, rather than be disposed within the injection lumen 204. As such, none of the lumens in the tubular member 102 may function to house the return wire 132. In this alternative embodiment, the tubular member 102 and the return wire 132 may be co-extruded to embed or integrate the return wire 132 with the tubular member 102.

FIG. 6 shows a cross-sectional view of a second alternative embodiment of the bipolar sphincterotome 100 taken along line 4-4 in FIG. 1. In the second alternative embodiment, the tubular member 102 includes a lumen 602 having a single function or purpose to house the return wire 132.

The tubular member 102 may be made of various materials or combinations of materials including, but not limited to, fluoropolymer materials such as polytetrafluoroethylene (PTFE) or perfluoroalkoxy (PFA), polyethylene, nylon, or fluorinated ethylene, as examples. Where the tubular member is made of a fluoropolymer material such as PTFE or PFA, to optimally adhere the conductive ink portion 126 to the fluoropolymer tubular member 102, a primer ink or base ink may be adhered or applied to the tubular member 102 before the conductive ink is applied. The primer ink may have characteristics or qualities that enable the primer ink to be adhesive to both the fluoropolymer material and to the conductive ink. The conductive ink may then be applied over the primer ink. The primer ink may enhance or increase the adhesiveness or bond between the fluoropolymer tubular member 102 and the conductive ink 126, which may prevent or reduce the ability for the conductive ink to be rubbed off or otherwise removed from tubular member 102. Additionally, the conductive ink and/or the primer ink may be applied or deposited on the tubular member in any of various ways, such as spraying, pad printing, rolling, brushing, dipping, or electroplating, as examples.

Figure 7:
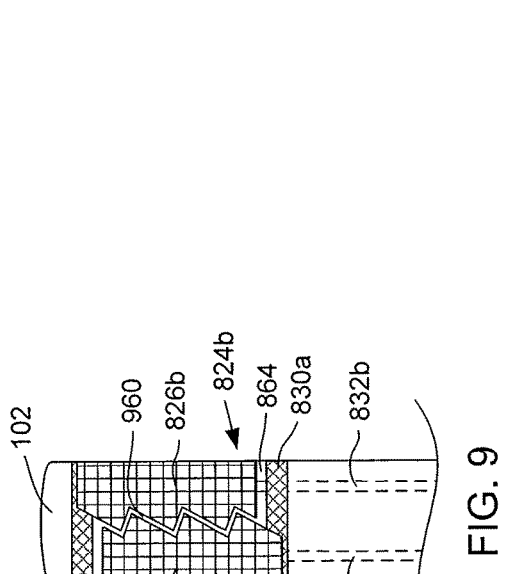
FIG. 7. shows a side view of the distal portion of the bipolar sphincterotome of FIG. 1, where the return path is a single return path.

In some example embodiments, the return path 124 may include a single return path. For these example embodiments, the conductive ink portion 126 may include a single, continuous portion electrically coupled to a single return wire 132. FIG. 7 shows a side view of an example embodiment of the distal portion 104 from an angle showing most if not all of the conductive ink portion 126, where the return path 124 is a single return path.

In alternative example embodiments, the return path 124 may include multiple, such as two, return paths. The multiple return paths may be electrically isolated or substantially electrically isolated from each other. Multiple return paths may be included to provide a safety feature for the bipolar sphincterotome 100. Some power sources 118 (FIG. 1) may be configured for dual return paths in that the power sources 118 may be configured to prevent output of the electrical current unless each of the return paths are in contact with the sphincter muscle or the surrounding tissue. This ensures adequate placement of the distal portion at the treatment site before the electrical current may be supplied from the power source 118. Additionally, if any of the return paths becomes disconnected, such as through fracture or burnout, the power source 118 may be configured to detect or recognize the disconnection and prevent the electrical current from being supplied to the treatment site.

Figure 8:
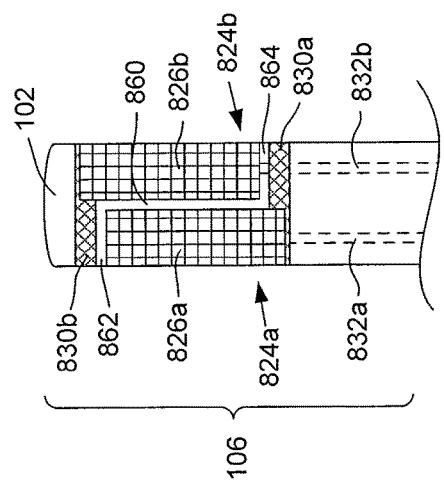
FIG. 8. shows a side view of an alternative embodiment of the distal portion of the sphincterotome of FIG. 1, where the return path includes two return paths and where a gap separating two conductive ink portions extends in a substantially straight direction.

FIG. 8 shows a side view of an example embodiment of the distal portion 106 from an angle showing most if not all of the conductive ink portion 126, where the return path includes a dual return path. The dual return path may include a first return path 824a and a second return path 824b. To form the first and second paths 824a, 824b, the conductive ink portion 126 may include two sub-portions or strips, including a first sub-portion 826a and a second sub-portion 826b. The first sub-portion 826a and the second sub-portion 826b may be electrically isolated from each other. The conductive ink making up the first and second sub-portions 826a, 826b may be deposited to form a gap or spacing 860 in between the first and second sub-portions 826a, 826b to electrically isolate the first and second sub-portions 826a, 826b from each other. In some example configurations, a width of the gap 860 may be about 0.040 inches, although other sizes for the width may be used.

The first and second sub-portions 826a, 826b may each be electrically coupled to a respective return wire. For example, the first sub-portion 826a may be electrically coupled to a first return wire 832a and the second sub-portion 826b may be electrically coupled to a second return wire 832b. In some example embodiments, the first and second sub-portions 826a, 826b may be electrically coupled to their respective return wires 832a, 832b at opposing ends of the sub-portions 826a, 826b. Additionally, the first and second sub-portions 826a, 826b may be electrically coupled to their respective return wires 832a, 832b in various ways, such as those described above. For example, as shown in FIG. 8, two metal cannulas 830a, 830b may be used to electrically couple the sub-portions 826a, 826b with their respective return wires 832a, 832b. The metal cannulas 830a, 830b may be disposed at opposing ends of the conductive ink portion 126 such that only one of the sub-portions 826a, 826b is coupled to each of the metal cannulas 830a, 830b. To do so, the second sub-portion 826b may distally extend past the first sub-portion 826a so that the second sub-portion 826b is electrically connected to the metal cannula 830b, and a gap 862 electrically isolates the second sub-portion 826b from the metal cannula 830a. Similarly, the first sub-portion 826a may proximally extend past the second sub-portion 826b so that the first sub-portion 826a is electrically connected to the metal cannula 830a, and a gap 864 electrically isolates the first sub-portion 826a from the metal cannula 830b. In other example embodiments, one or both of the metal cannulas 830a, 830b may be replaced with an opening in the tubular member 102 (such as the opening 150 shown in FIG. 1A). The conductive ink making up the first sub-portion 826a may extend into one of the openings to be electrically coupled with the first return wire 832a. Similarly, the conductive ink making up the second sub-portion 826b may extend into the other opening to be electrically coupled with the second return wire 832b.

The return wires 832a, 832b may be disposed within the tubular member in various combinations of the embodiments shown in cross-section in FIGS. 4-6. For example, one of the return wires 832a, 834b may be disposed within one of the lumens, such as the injection lumen, so that one of the lumens serves a dual purpose as described above. The other of the return wires 832a, 832b may be embedded as an integral component of the tubular member 102. Alternatively, one of the return wires 832a may be disposed within a lumen serving a dual purpose and the other return wire 832b may be disposed within a lumen having a sole purpose to house the return wire 832b. Alternatively, both of the return wires 832a, 832b may be embedded within the tubular member 102, or each of the return wires 832a, 832b may be disposed in respective lumens, each of which has a sole purpose of housing the return wire 832a or 832b. Various configurations are possible. In the tubular member 102, the return wires 832a, 832 may longitudinally extend parallel or substantially parallel to each other.

Figure 9:
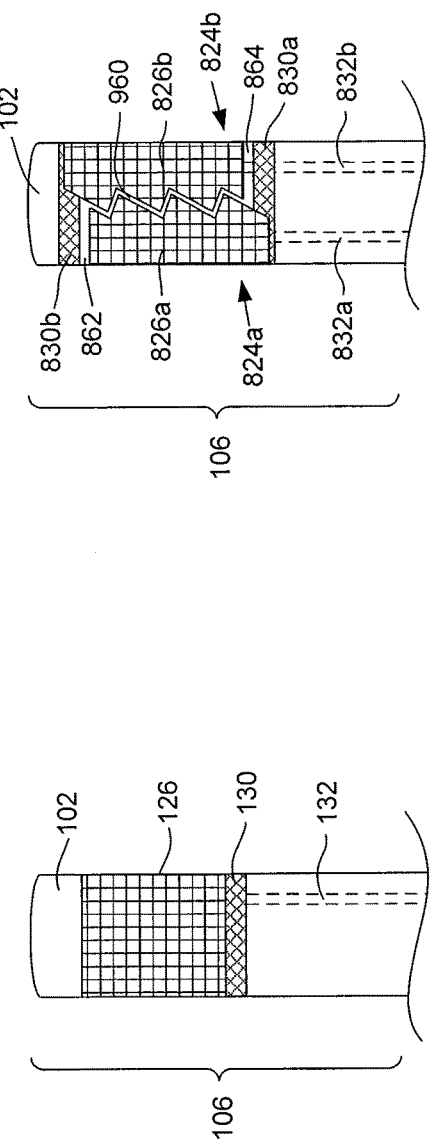
FIG. 9. shows a side view of a second alternative embodiment of the distal portion of the sphincterotome of FIG. 1, where the return path includes two return paths and where the gap has a zig-zag pattern.
Figure 10:
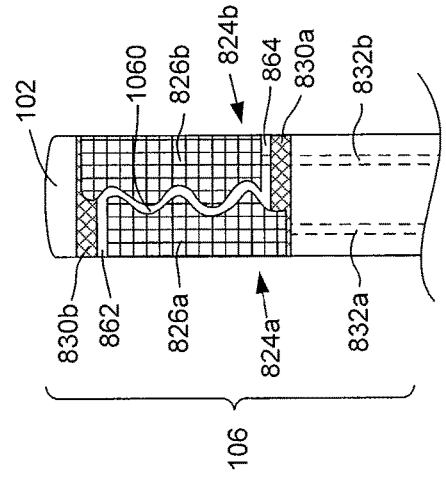
FIG. 10. shows a side view of a third alternative embodiment of the distal portion of the sphincterotome of FIG. 1, where the return path includes two return paths and where the gap has a sinusoidal pattern.

In one example configuration, as shown in FIG. 8, the gap 860 separating and electrically isolating the first and second sub-portions 826a, 826b may longitudinally extend along the outer surface of the distal portion in a straight or substantially straight direction. In alternative configurations, the gap may longitudinally extend in a non-straight manner. For example, as shown in FIG. 9, a gap 960 may have a zig-zag pattern. As another example, referring to FIG. 10, the gap 1060 may have a sinusoidal pattern. Various other patterns may be used for the gap, such as helical or spiral, as examples. Alternatively, the gap may not necessarily have a pattern, but may extend in a generally non-straight manner along the outer surface of the distal portion 106. Configuring the gap to extend in a non-straight manner or have a non-straight pattern may be advantageous over configurations where the gap extends straightly in that the non-straight configurations may facilitate contact for both the first and second sub-portions of the conductive ink with the sphincter muscle or surrounding tissue.

Referring back to FIG. 1, the return cabling 144 may be configured to connect to various types or configurations of the power source 118 and/or of the return port 146 of the power source 118. In many situations, the power source 118 used to connect to the bipolar sphincterotome 100, may have been configured, such as when manufactured, to connect to and/or receive return cabling for monopolar sphincterotomes, which may use a solid neutral electrode or a split neutral electrode as part of the return path. Some power sources 118 may be configured to receive and/or connect to a single return path (e.g., a monopolar sphincterotome that uses a solid neutral electrode), two return paths (e.g., a monopolar sphincterotome that uses a split neutral electrode), or both.

For the bipolar sphincterotome configurations, the return cabling 144 electrically coupling the return path 124 to the return port 146 of the power source 118 may be configured in various ways to accommodate both the single and dual path configurations of the bipolar sphincterotome 100 as well as a power source 118 configured to recognize a solid neutral electrode, a split neutral electrode, or both.

Referring to FIG. 11, where the bipolar sphincterotome 100 includes a single return path, to connect to a power source 118 that is configured to recognize a solid neutral electrode, the return cabling 144 may include a single wire 1102 that is connected to a single return wire 132. The wire 1102 may proximally terminate at a plug 1104 that is adaptable to connect and electrically couple the wire 1102 to the return port 146 of the power source 118.

Referring to FIG. 12, where the bipolar sphincterotome 100 includes two return paths, to connect to a power source 118 that is configured to recognize a split neutral electrode, the return cabling 144 may include two wires 1202, 1203 electrically isolated from each other. One of the wires 1202 in the return cabling 144 may be connected to one of the return wires 1232a, and the other wire 1203 in the return cabling 144 may be connected to the other return wire 1232b. Each of wires 1002, 1003 may proximally terminate at a plug 1204 that is adaptable to connect and electrically couple the wires 1202, 1203 to the return port 146.

Figure 14:
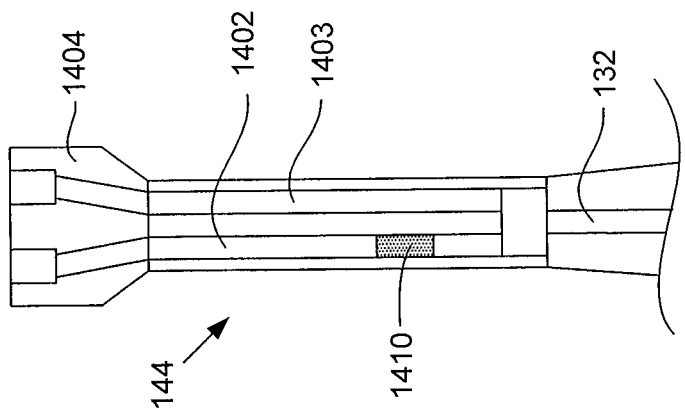
FIG. 14 shows a cross-sectional view of a third alternative embodiment of the cabling of FIG. 11, where the cabling includes two wires, and where one of the wires includes a resistive element.

For some power sources 118, the return port 146 may be configured to connect to two return paths, even though the power source 118 may be configured to recognize a solid neutral electrode. For these configurations, the return cabling 144 may include two wires that are configured so that the power source 118 recognizes a solid neutral electrode. Referring to FIG. 13, where the bipolar sphincterotome 100 includes a single return path, to connect to a power source 118 that is physically configured to receive two return paths but is also configured to recognize a solid neutral electrode, the return cabling 144 may include two wires 1302, 1303 that are shorted together at a distal end of the wires 1302, 1303, where they also may be connected to a proximal end of the single return wire 132. Each of wires 1302, 1303 may proximally terminate at a plug 1304 that is adaptable to connect and electrically couple the wires 1302, 1303 to the return port 146. For this configuration, the power source 118 may determine or recognize a nominal resistance between the two return paths, just as it would for a solid neutral electrode.

Where the return port 146 is configured to connect to two return paths, and the power source 118 is configured to recognize a split neutral electrode, a resistance may be included in one of the wires in the return cabling 144 where the return path 124 of the bipolar sphincterotome includes a single return path. Referring to FIG. 14, a resistive element or resistor 1410 may be added to or included in one of wires 1402, 1403 of the return cabling 144 so that a resistance exists between the two wires 1402, 1403. The wires 1402, 1403 may then be connected together at their distal ends, where they may be connected to the single return wire 132. The resistance chosen for the resistive element 1410 may be in range that the power source 118 may be configured to measure or recognize the bipolar sphincterotome 100 as using a split neutral electrode. In some examples, the range may be about 5-150 Ohms, although other resistances may be used depending on the power source 118. The value of the resistance may be optimized to work for multiple or various types of power sources 118.

Alternatively, the resistance for the resistive element 1410 may be a value that may cause the power source 118 to recognize the bipolar sphincterotome 100 as using either a solid neutral electrode or a split neutral electrode. Some power sources 118 are configured to use an upper limit for resistance that the power source 118 may accept to recognize a solid neutral electrode, while also having a lower limit for resistance that the power source 118 may accept to recognize a split neutral electrode. For these power sources 118, if there is an overlap between the upper and lower limits, the resistance for the resistive element 1410 may be chosen in the overlap, and no errors may be identified by the power source 118 whether the power source 118 is set to recognize either a solid neutral electrode or a split neutral electrode.

Figure 15:
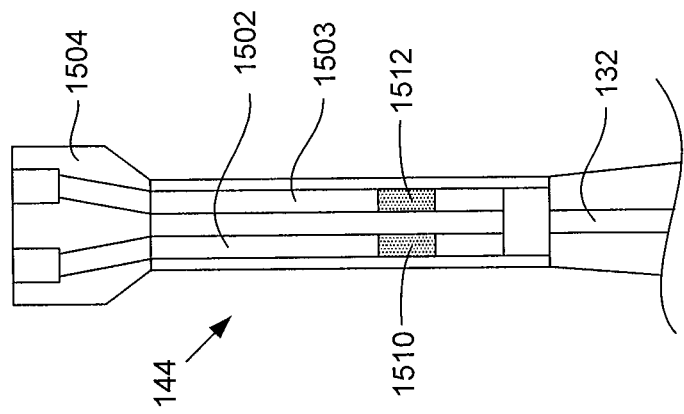
FIG. 15 shows a cross-sectional view of a fourth alternative embodiment of the cabling of FIG. 11, where the cabling includes two wires, and where each of the wires includes a resistive element.

In an alternative embodiment, resistive elements may be included in both of the wires in the cabling. Referring to FIG. 15, a resistive element 1510 may be included in a wire 1502, and a resistive element 1512 may be included in a wire 1503 of the return cabling 144. The sum of the resistances of the resistive elements 1510, 1512 may be equal to a resistance of a single resistive element where only one of the wires includes a resistive element (e.g., resistive element 1410 shown in FIG. 14). Additionally, the resistances of the resistive elements 1510, 1512 may be the same or substantially the same. Resistive elements 1510, 1520 may be included in both of the wires 1502, 1503 in order to split the power between the two wires 1502, 1503. Heat generated by the two resistive elements 1510, 1512 may be reduced, compared to the single resistive element configuration shown in FIG. 14, because less power may be drawn through each of the resistive elements 1510, 1512. Using two resistive elements 1510, 1512 may also minimize or eliminate polarity in the return path, which may pose safety or performance problems for the sphincterotome.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A bipolar sphincterotome to perform a sphincterotomy at a treatment site, the bipolar sphincterotome comprising:
   an elongate tubular member;
   a cutting wire disposed within the elongate tubular member;

a wire guide lumen disposed and longitudinally extending within the elongate tubular member, the cutting wire disposed outside of the wire guide lumen; and a return path comprising:
- a conductive material portion covering an outer surface at a distal portion of the elongate tubular member, the conductive material portion having a circumferential disposition about the outer surface that provides visual access to the wire guide lumen; and
- a return wire electrically coupled to the conductive material portion, the return wire disposed within the elongate tubular member and outside of the wire guide lumen, and
- wherein the circumferential disposition comprises the conductive material portion being circumferentially offset by a non-zero angle relative to a circumferential orientation that is perpendicular to a radial orientation of a cutting edge of the cutting wire to provide visual access to the wire guide lumen.

2. The bipolar sphincterotome of claim 1, further comprising:
a conductive cannula disposed about the outer surface of the elongate tubular member, the conductive cannula electrically coupling the conductive material portion to the return wire.

3. The bipolar sphincterotome of claim 2, wherein at least a portion of the conductive material portion is further disposed over at least a portion of the conductive cannula to electrically couple the conductive material portion to the return wire.

4. The bipolar sphincterotome of claim 3, further comprising:
a shrink tube disposed over the conductive cannula.

5. The bipolar sphincterotome of claim 2, further comprising:
a tube having an inner surface coated with a conductive material to electrically couple the conductive material portion with the conductive cannula.

6. The bipolar sphincterotome of claim 1, further comprising:
a skive in the elongate tubular member extending from the outer surface to a location within the elongate tubular member that is in communication with a distal end of the return wire,
wherein the conductive material portion extends within the skive to be electrically coupled with the return wire.

7. The bipolar sphincterotome of claim 1, further comprising:
a lumen, other than the wire guide lumen, disposed and longitudinally extending within the elongate tubular member,
wherein the lumen has two or more functions, one of the two or more functions being to house the return wire.

8. The bipolar sphincterotome of claim 7, wherein the lumen comprises an injection lumen, wherein a second function of the two or more functions is to deliver contrast to a treatment site.

9. The bipolar sphincterotome of claim 1, wherein the return wire is embedded within the elongate tubular member.

10. The bipolar sphincterotome of claim 1, further comprising:
a lumen, other than the wire guide lumen, disposed and longitudinally extending with the elongate tubular member,
wherein the lumen has a single function, the single function being to house the return wire.

11. The bipolar sphincterotome of claim 1, wherein the elongate tubular member is made of a substantially clear material.

12. The bipolar sphincterotome of claim 1, wherein the conductive material portion distally extends past an anchor point where a distal end of the cutting wire is fixedly attached to the elongate tubular member.

13. The bipolar sphincterotome of claim 1, wherein a thickness of the conductive material portion is less than or equal to about 500 micrometers, wherein the conductive material portion comprises conductive ink particles having sizes in a range of about 3 to about 30 micrometers, and wherein the conductive material portion has a longitudinal resistance of less than or equal to about 20 Ohms.

14. The bipolar sphincterotome of claim 1, further comprising:
cabling that electrically couples the return path to a return port of a power source,
wherein the cabling comprises a first wire and a second wire, the first and second wires being shorted together at distal ends of the first and second wires, and
wherein the first and second wires are connected to a proximal end of the return wire at the distal ends.

15. The bipolar sphincterotome of claim 14, wherein a resistive element is included in one of the first wire or the second wire, wherein a resistance value of the resistive element is configured to cause the power source to recognize the return path of the bipolar sphincterotome as including a split neutral electrode.

16. The bipolar sphincterotome of claim 14, wherein a resistive element is included in one of the first wire or the second wire, wherein a resistance value of the resistive element is configured to cause the power source to recognize the return path of the bipolar sphincterotome as including a solid neutral electrode or a split neutral electrode.

17. The bipolar sphincterotome of claim 14, wherein a first resistive element is included in the first wire, and wherein a second resistive element is included in the second wire, wherein a sum of a resistance value of the first resistive element and a resistive value of the second resistive element is configured to cause the power source to recognize the return path of the bipolar sphincterotome as including a solid neutral electrode or a split neutral electrode.

18. The bipolar sphincterotome of claim 1, wherein the conductive material portion comprises a conductive ink portion.

19. A bipolar sphincterotome comprising:
an elongate tubular member;
a cutting wire disposed within the elongate tubular member;
a wire guide lumen disposed and longitudinally extending within the elongate tubular member; and
a return path comprising:
- a conductive ink portion covering an outer surface at a distal portion of the elongate tubular member; and
- a return wire electrically coupled to the conductive ink portion,
wherein a circumferential disposition of the conductive ink portion about the outer surface of the distal portion comprises the conductive ink portion being circumferentially offset by a non-zero angle relative to a circumferential orientation that is perpendicular to a radial orientation of a cutting edge of the cutting wire.

20. A bipolar sphincterotome to perform a sphincterotomy at a treatment site, the bipolar sphincterotome comprising:
an elongate tubular member;

a cutting wire disposed within the elongate tubular member;
a wire guide lumen disposed and longitudinally extending within the elongate tubular member, the cutting wire disposed outside of the wire guide lumen;
a return path comprising:
  a conductive material portion covering an outer surface at a distal portion of the elongate tubular member, the conductive material portion having a circumferential disposition about the outer surface that provides visual access to the wire guide lumen; and
  a return wire electrically coupled to the conductive material portion, the return wire disposed within the elongate tubular member and outside of the wire guide lumen; and
a conductive cannula disposed about the outer surface of the elongate tubular member, the conductive cannula electrically coupling the conductive material portion to the return wire,
wherein the conductive material portion comprises a conductive ink portion.

* * * * *